United States Patent [19]
Tsai et al.

[11] Patent Number: 6,140,118
[45] Date of Patent: Oct. 31, 2000

[54] AVIAN BLASTODERMAL CELL LINES

[75] Inventors: Herng Tsai, East Lansing; Henry D. Hunt, Okemos; Larry D. Bacon, Williamston, all of Mich.; Bernard C. Wentworth; Alice L. Wentworth, both of Madison, Wis.

[73] Assignees: Wisconsin Alumni Research Foundation, Madison, Wis.; The United States of America as represented by the Department of Agriculture, Washington, D.C.

[21] Appl. No.: 09/372,702

[22] Filed: Aug. 11, 1999

[51] Int. Cl.$^7$ ........................................... C12N 5/00
[52] U.S. Cl. ............................................. 435/325
[58] Field of Search ............................................. 435/325

[56] References Cited

U.S. PATENT DOCUMENTS

| | | | |
|---|---|---|---|
| 5,340,740 | 8/1994 | Petitte et al. | 435/349 |
| 5,656,479 | 8/1997 | Petitte et al. | 435/349 |

OTHER PUBLICATIONS

H. Tsai, "Blastodermal Cells: A Way Into Avian Gernome," University of Wisconsin Thesis (1995).

M. Federspiel et al., "Experimentally Introduced Defective Endogenous Proviruses are Highly Expressed in Chickens," *J. Virol.*, 65: 313–19 (1991).

J. Petitte et al., The Origin of the Avain Germ Line and Transgenesis in Birds, 76 *Poult. Sci.* 1084–92 (1997).

R. Etches et al., Strategies for the Production of Transgenic Chickens, 62 *Methods Mol. Biol.* 433–50 (1997).

M. Naito et al., "Expression of exogenous DNA in the gonads of chimaeric chicken embryos produced by transfer of primordial germ cells transfected in vitro and subsequent fate of the introduced DNA," 113 *J. Reprod. Fertil.* 137–43 (1998).

M. Nakamura et al., "Behavior of Chick Primordial Germ Cells Injected into the Blood Stream of Quail Embryos," 67 *Okajimas Folia Anat.* Jpn. 473–7 (1991).

J. Petitte et al., "Production of somatic and germline chimeras in the chicken by transfer of early blastodermal cells," 108 *Develop.* 185–9 (1990).

A. Hahnel et al., "Cell Surface Markers of Mouse Primordial Germ Cells Defined by Two Monoclonal Antibodies," 15 *Gamete Research* 25–34 (1986).

L. Urven et al., "Analysis of germ line development in the chick embryo using an anti–mouse EC cell antibody," 103 *Develop*.299–304 (1988).

A. Romanoff et al., *The Avian Embryo: Structural And Functional Development*, 1051–1079, The Macmillan Company, New York (1960).

H. Eyal–Giladi, et al., "From Cleavage to Primitive Streak Formation: A complementary Normal Table and a New Look at the First Stages of the Development of the Chick," 49 *Develop. Bio.* 321–337 (1976).

F. Villars et al., "Ability of various inserts to promote endothelium cell culture for the establishment of coculture models," 12 *Cell Biol. Toxical.* 207–214 (1996).

R. Penza et al. "Dil as a Marker for Cellular Transplantation into Solid Organs," *BioTechniques*, 13:580–587 (1992).

J.E. Fulton et al., "Functional analysis of avian class I (BFIV) glycoproteins by epitope tagging and mutagenesis in vitro," *Eur. J. Immunol.*, 25:2069–2076 (1995).

M.M. Perry, "A complete culture system for the chick embryo," *Nature*, 331:70–72 (Jan. 1988).

S. Kochav et al., "From Cleavage to Primitive Streak Formation: A Complementary Normal Table and a New Look at the First Stage of the Development of the Chick," *Develop. Biol.*, 79:296–308 (1980).

*Primary Examiner*—Robert A. Schwartzman
*Assistant Examiner*—Andrea Ousley
*Attorney, Agent, or Firm*—Quarles & Brady LLP

[57] ABSTRACT

Disclosed herein are cultures of undifferentiated avian primordial germ cells/blastodermal cells. The cultures are capable of maintaining their undifferentiated characteristic and also their capability of expressing the EMA-1 epitope for extended periods when cultured in the presence of an isolate from avian navel (e.g. turkey navel extract). Methods of culturing such cultures using avian navel extracts, and culture media containing avian navel extract are also disclosed. Recombinant birds derived from these cultures are also disclosed. These cultures can be frozen for long-term preservation of germ line genomes.

11 Claims, No Drawings

AVIAN BLASTODERMAL CELL LINES

STATEMENT REGARDING FEDERALLY SPONSORED RESEARCH

This invention was made with United States government support awarded by the following agency: USDA 96-CRHR-0-6055. The United States Government has certain rights in this invention.

CROSS REFERENCES TO RELATED APPLICATIONS

BACKGROUND OF THE INVENTION

The present invention relates to immortalized blastodermal avian cell lines as well as techniques for creating such lines and materials used in such methods. Such cell lines are desirable for creating transgenic birds and preserving germ line genomes.

Transgenic technology is a powerful tool for improving the commercial value of plants (e.g. enhancing their disease and herbicide resistance). However, attempts to improve the genetic characteristics of animals have lagged behind plants, with most of the early emphasis being on using animals as bioreactors to produce synthetic human pharmaceuticals. There has been little progress in improving the genetic quality of farm animals to date using transgenic techniques.

A particular impetus for such efforts is present in the poultry (e.g. chickens, ducks, geese, turkey, etc.) industry where there is typically high density rearing which results in increased risk of infection by diseases such as Marek's disease and avian leukosis. Commercial breeders have therefore sought to select (using natural breeding techniques) for poultry having increased disease resistance.

There had been some thought of trying to introduce foreign genes into poultry breeding lines for purposes of increasing disease resistance. For example, a germ line was infected with a mutant ALV virus that increased resistance to a particular subgroup of avian leukosis virus. See M. Federspiel et al. 65 J. Virol. 313-19 (1991). The disclosure of this publication and of all other publications referred to herein are incorporated by reference as if fully set forth herein.

Attempts were also made to introduce selected foreign genes by cloning them into a retrovirus vector (e.g. reticuloendotheial virus or avian leukosis virus), injecting the recombinant virus into fertile eggs, allowing the virus to infect the developing embryo (e.g. primordial germ cells) thereby creating a chimeric gonad or ova, and using the resultant recombinant to try to introduce a foreign gene into the progeny. However, the poultry industry has been reluctant to commercially use this technology as the virus (in its natural state) is a pathogen, even variant replication competent virus vectors can sometimes induce tumors, and replication incompetent variants require high or repeated dosages. Also, even replication defective virus constructs can pose some risk of recombining with endogenous virus envelope and becoming replication competent. Further, these vectors are currently limited to DNA inserts of relatively small size (e.g. two kilobases or less).

There have also been attempts to inject foreign DNA into the undeveloped fertilized ovum after it is surgically removed from the hen. See M. Perry, 331 Nature (1998). However, this approach required incubating the developing embryo in a series of surrogate containers. Further, it required specialized laying flocks and extensive practice to obtain the needed surgical and technical skills.

A technically less demanding prior art approach involved the introduction of foreign DNA into the embryo after the egg had been laid. See generally J. Petitte et al., 76 Poult. Sci., 1084–92 (1997); R. Etches et al., 62 Methods Mol. Biol., 433–50 (1997); M. Naito et al., 113 J. Reprod. Fertil, 137–43 (1998); M. Nakamura et al., 67 Okajimas Folia Anat Jpn., 473–7 (1991); J. Petitte et al., 108 Development, 185–9 (1990); and U.S. Pat. Nos. 5,340,740 and 5,656,479, J. Petitte et al.

This involved the injection of genetically modified embryonic cells or primordial germ cells into the blastoderm either shortly after lay or about 48 hours later when the primordial germ cells are beginning their migration to the gonadal analagen. In this approach, blastodermal cell cultures were created which retained their ability to differentiate into functional ova or spermatozoa producing cells when incorporated into the developing embryo.

Blastodermal cell cultures of this type can be genetically modified and then injected into recipient embryos. The recipient embryos would typically have been previously modified by gamma irradiation to debilitate the endogenous primordial germ cells and give the injected cells a selection advantage in homing into the gonadal analagen. The modified cells would then mature and produce spermatozoa or ova capable of transmitting the transgene to at least the next generation (and preferably other future generations).

A key to the success of this technique is the ability to expand the embryonic blastodermal cells in culture while inhibiting their differentiation. Several groups have therefore developed culture techniques based on the addition of various cloned factors and feeder cells that allow short term (a few days to approximately two weeks) expansion of the embryonic cells while retaining their primordial germ cell phenotype. These cultured cells have been successful in producing germ line chimeras, but most attempts to express transfected DNA as transgenes using this system have been unsuccessful.

Another approach relied on the use of culture medium containing toxins.

Thus, it can be seen that there is a need for improved culture conditions for avian blastodermal cell cultures.

BRIEF SUMMARY OF THE INVENTION

In one aspect the present invention provides a culture of undifferentiated avian (preferably poultry such as turkey, duck, geese and chicken) blastodermal cells expressing the EMA-1 epitope, wherein the culture is capable of maintaining its undifferentiated characteristic and its capability of expressing the EMA-1 epitope for extended periods (preferably for more than six months) when cultured in the presence of isolate from avian navel (e.g. an isolate from embryonic avian navel).

In another aspect the invention provides a method of producing a sustained culture of undifferentiated blastodermal cells capable of expressing the EMA-1 epitope. One collects avian cells from an avian blastoderm prior to the formation of a primitive streak. One then cultures the avian cells in the presence of avian navel isolate such as turkey navel extract.

In yet another form the invention provides a medium for culturing avian (e.g. poultry) blastodermal cells comprising the avian navel isolate. The culture medium also preferably contains other ingredients present in standard blastodermal cultures.

In still another form the invention provides a method of preserving an avian germ line genome. This is achieved by freezing one of the above cultures.

Another form of the present invention provides recombinant birds derived from such cultures.

By culturing blastodermal cells with culture medium containing avian navel isolate, a sustained culture can be obtained containing undifferentiated primordial germ cells. This provides an efficient culture for creating recombinant cells.

Resulting recombinant germ cells are useful to produce recombinant birds and to preserve germ line genome. Furthers it seems likely that such recombinant birds will be able to pass these foreign traits to their offspring.

The objects of the present invention therefore include providing:

(a) sustained avian primordial germ cell cultures that can remain undifferentiated for extended periods without the need for a feeder layer or toxins;

(b) recombinant birds derived from such cell cultures;

(c) methods for creating such cultures;

(d) methods for preserving genomes by freezing such cultures; and (e) culture media useful in practicing such methods.

These and still other objects and advantages of the present invention will be apparent from the description of the preferred embodiments that follows. However, the claims should be looked to in order to judge the full scope of the invention.

DETAILED DESCRIPTION

General Overview

We have provided a stable avian blastodermal cell ("BDC") culture system which requires no feeder layer or toxins and that can maintain viable BDC for more than six months. The cultured BDC express the EMA-1 epitope which is a marker of primordial germ cells. See A. Hahnel et al., 15 Gamete Research 25–34 (1986) and L. Urven et al., 103 Develop. 299–304 (1988). Cultured cells produced by this technique were able to contribute to hematopoietic cells and various other cell types when they were transfected and then inserted into recipient chicken embryos.

Materials

The source for both donor blastodermal cells and recipient fertile eggs was the Avian Disease and Oncology Laboratory (ADOL). We used their lines 0 (MHC=$B^{21}B^{21}$), C (MHC=$B^{12}B^{12}$), $7_1$ (MHC=$B^2B^2$), $15I_5 \times 7_1$ (MHC=$B^2B^{15}$), N (MHC=$B^{21}B^{21}$), P(MHC=$B^{19}B^{19}$), in part because these lines were known to have been maintained free of common pathogen viruses.

Our culture media were as follows. Serum free and protein free hybridoma medium (SFPF, #S2897) was used to culture Line 0 BDC.

L-15 Leibovitz Medium/McCoy's 5A Modified Medium (L/M at 1:1 ratio, #L4386, #M4892) was used to culture Line 0, Line $7_1$, and $15I_5 \times 7_1$.

Dulbecco's modified eagle's medium/ham's nutrient mixture (DMEM/F-12, #D0547) was used for Line C.

Minimum essential medium eagle (MEM, #M0644) was used for Line P.

More generically, such media typically contain water, inorganic salts, vitamins, amino acids, buffers, glucose, nucleotide precursors/nucleotides, lipids, TCA cycle intermediates, and various minor additives.

Penicillin and Streptomycin (Pen/Strep) at 1,000U/ml final concentration were also used in all media in order to inhibit bacterial cell growth.

Forskolin (#F6886 or #F3917) was also added to facilitate BDC growth in Line C (20 ug/100 ml final concentration).

All the above culture medium reagents were purchased from Sigma Chemical Co., St Louis, Mo., and fetal bovine (calf) serum (FBS, Gibco BRL Life Technologies, Grand Island, N.Y.) was added to all media at 20% final concentration.

Turkey navels were obtained from piping embryos. Each navel was excised (0.7–1 cm diameter) from abdominal area surrounding the umbilical cord attachment. Any remaining umbilical cord was removed. The navels were pooled in ice cold medium without serum (one navel per two ml of medium), homogenized via a tissue grinder in an ice bath, freeze-thawed three times, and centrifuged at 25,000×g at 4° C. for 30 minutes. The ice cold medium used for this purpose was, for example, serum free and protein free hybridoma medium (SFPF, #S2897). The key feature is that the extracting liquid contained water as the relevant isolate is water soluble.

The supernatant was retained and sterile filtered through a 0.22 um membrane (to remove particles greater than that size), aliquoted at 1 ml per vial and stored at −20° C. This sterile filtered turkey navel extract ("TNE") was freshly added to the cell culture at 400 ul TNE/10 ml medium (equivalent of two navels per 100 ml of medium).

When an avian embryo is about to hatch the yolk sac begins to retract into the embryo's body cavity through a small opening in the abdominal area (conventionally known as the navel). This opening will heal within minutes after yolk sac retraction. See A. Romanoff et al., *The Avian Embryo: Structural And Functional Development*, 1051–1079, The Macmillan Company, New York (1960).

We believe that the cells in avian navel tissue secrete growth/healing factor(s) to speed up the closure of the navel. If the navel is not fully healed, the hatched chick is susceptible to infection in the early post-hatch days. We discovered that these factors are useful for our culture medium.

As an optional additive, we used chicken embryo extract. Seven day old chicken embryos were placed in serum free and protein free hybridoma medium (SFPF, #S2897) medium, homogenized in an ice bath, freeze-thawed three times, and centrifuged at 25,000×g at 4° C. for 30 minutes. The supernatant was sterile filtered through 0.22 um membrane. The sterile chicken embryo extract was aliquoted at the equivalent of approximately one embryo (depends on the volume of the extract obtained) per vial and stored at −20° C. The extract was optionally added at the equivalent of one embryo per 100 ml of culture medium. This additive is believed to enhance cell proliferation.

The EMA-1 monoclonal antibody is described in A. Hahnel et al., 15 Gamete Research 25–34 (1986). It reacts with primordial germ cells. The EMA-1 epitope is regarded as a marker of avian primordial germ cells. EMA-1 antibody was obtained from U. of Iowa Developmental Studies Hybridoma Bank.(Iowa City, Iowa).

As a transfection solution we used medium 199 (M 199, #M7667) with 2.5% FBS and 1% Pen/Strep., hepes buffered saline 2× (HBS 2×) solution: 140 mM NaCl, 1.5 mM $Na_2HPO_4$, 50 mM hepes (#H9136, Sigma) at pH 7.05, 2M $CaCl_2$ in deionized $H_2O$ ($dH_2O$).

As an example vector we used a plasmid containing the marker protein "green fluorescence protein" (pEGFP, CLONETECH laboratories, Inc., Palo Alto, Calif.). We also used other vectors containing other foreign genes of interest. See e.g. ppZeoBFIVprom/FLAG/B21 as described in J. Fulton et al., 25 Eur. J. Immunol. 2069–2076 (1995).

For purposes of encouraging cell dissociation during various stages of culturing, collagenase (#17103, GibcoBRL Life Technologies) was diluted at 0.2 mg/ml in L/M medium without serum. A cell scraper-rubber policeman (#14-105B, Fisher Scientific, Pittsburgh, Pa.) was used to remove cells from the culture insert.

To render an embryo recombinant, we needed access to the egg in the interior of the shell of a recently laid (18 hour) egg. Because this involved opening the shell, we needed to have available patch sections of shell membranes. For this purpose, eggs were cracked open and the contents were discarded. The shell membrane was peeled off the shell and placed in a sterile 150×20 mm culture plate containing 1% Pen/Strep in phosphate buffered saline. The shell membrane was cut into pieces approximately 2 $cm^2$ in size.

Methods

A. Creating Primordial Germ Cell Lines

We created a culture of blastodermal cells in accordance with the present invention. The central part (area pellucida) of a blastoderm from stage IX–XIV (H. Eyal-Giladi, et al., 49 Develop. Bio. 321–337 (1976)) unincubated fertile eggs was cut with micro dissecting scissors (#11-1020, Biomedical Research Instruments, Inc., Rockville, Md.), removed via micro dissecting forceps (#10-1605, BRI), and placed into five ml of culture medium. Approximately 30 blastoderms were pooled together and gently passed several times through a 22G needle fitted to a 3 ml syringe to disperse the cells.

The cells were then deposited into a cell culture insert (F. Villars et al., 12 Cell Biol. Toxicol. (1996)). For this purpose we used Transwell porous cell culture inserts, 75 mm diameter, 0.4 um pore size, polycarbonate membrane, 3419, Corning Incorporated, Corning, N.Y.

An additional 15 ml of culture medium containing fresh turkey navel extract (with optional chicken embryo extract) was added to the culture which was incubated at 37° C. The BDC attached to the insert membrane in two days and reached confluency within a week.

An example of a suitable culture medium contained 82% hybridoma medium, 15% fetal calf serum, 1% Pen/Strep, extract from two turkey navels, and extract from one chicken embryo.

Upon confluency, the BDC were scraped off the culture insert with a cell scraper and diluted in fresh medium at a 1:2 to 1:3 ratio every five to seven days. At various passages there was sensitivity to trypsin or collagenase treatment, so enzyme dissociation was avoided during at least primary and early subcultures.

We then tested these cells for the expression of EMA-1 epitope at various times of culture. Such testing can be achieved by a variety of standard techniques. As one example, one can remove the media from the culture (leaving the culture in plated form). The culture can then be washed three times with PBS. One can then add EMA-1 antibody solution to the plate. The system can then be incubated for 15 minutes at room temperature (or for a half hour at 4 degrees centigrade).

The EMA-1 solution is then removed from the plate, followed by three further washes with PBS. One then adds FITC conjugated goat anti-mouse IgM antibody and incubates at room temperature for fifteen minutes. Following three additional washes with PBS one views the plate under a UV filter equipped microscope. Bound antibody will be visible and be indicative of EMA-1 expression.

B. Freezing.

The resulting blastodermal cell lines could not be successfully frozen at early stages of culture due to the high content of lipid granules in cells. However, after two months in culture, we could successfully freeze, store and then reculture.

In this regard, the blastodermal cells were removed from the culture insert with collagenase dissociation and resuspended in freezing medium in a cryovial. The vial was frozen in a styrofoam box overnight at −70° C. and then stored at −70° C. for short term storage. For longer storage we believe that the cells should be kept in liquid nitrogen.

As a cell freezing medium we used hybridoma culture medium 50% (without chicken embryo extract or turkey navel extract), along with 10% dimethyl sulfoxide. (DMSO, #D2650, Sigma Chemical) and 40% fetal calf serum. From freezing and thawing experiments we have determined that BDC can be successfully stored frozen after two months in culture.

C. Transfection

We then used vectors to render our culture cells recombinant. We began with transfection using a modified calcium phosphate precipitation procedure. Blastodermal cells used for transfection had been cultured from two to six months. Twenty ug of test plasmid/vector in 20 ul of $dH_2O$, 120 ul of 2M $CaCl_2$, 860 ul of $dH_2O$ and 1 ml of HBS 2× were added to a Falcon 12×75 mm sterile polystyrene round bottom tube (#2058, Becton Dickinson Labware, Lincoln Park, N.J.).

Air was bubbled through the tube for 1 minute using a 1 ml pipette. The tube was incubated at room temperature for 30 minutes. This plasmid solution (2 ml) was then added to the culture plate in which the culture medium was replaced with M199 containing 2.5% FBS, and incubation was continued for eight hours at 37° C. Then, the M199 medium was discarded, the plate was washed with M199 medium, and the original culture medium was added back to the culture plate. An important aspect of this protocol is the repeated transfection of the blastodermal cell cultures in the absence of chemical selection. This greatly enhances the survival of these fragile cells while increasing the transfection efficiency to 30%. D. Injection Of Foreign Host Embryo Egg shell of a newly-laid fertilized egg was sanitized with 70% alcohol and the air cell was defined and traced utilizing an egg candler. After 18 hours of incubation the eggs were removed from the egg incubator (Jamsway, forced air type) to room temperature. A one cm diameter hole was ground through the shell in the air cell area using a belt sander (Type 3, #7451, 3"×24" belt size, amps 5.2, belt FT./minute 1200, Black & Decker In., Towson, Md. 21210). The shell membrane was removed with a blunt end forceps.

Twenty ul of medium containing 10,000 DiI saturated or transfected BDC was injected into the germinal crescent area of the chick embryo via a microcapillary needle pipette with about a 40 um pore size. DiI [DII: 1,1'-dioctadecyl-3, 3,3,3'-tetra-methylindo-carbocyanine perchlorate; diI-$C_{18}$-(3)] (Molecular Probes, Eugene, Oreg.) was dissolved in 100% DMSO. A stock solution of 2.5 mg/ml was prepared and diluted into culture medium at 2.5 ug/ml final concentration to stain blastodermal cells in a culture plate for 8 hours during incubation at 37° C. The culture plate was washed five times with PBS after removal of DiI containing medium.

Note that methods exist to detect DiI-stained cells in tissues. For example, seven day old embryonic gonads could be removed from embryos and fixed in 4% paraformaldehyde at 4° C. for 8 hours, then in 5% sucrose in PBS overnight at 4° C., followed by 30% sucrose in PBS for 8 hours at 4° C., prior to freezing at −70° C. Fluorescence microscopy was performed on 5 um cryosections. DiI can be visualized using rhodamine filters or narrow band filters (R. Penza et al., 13 Biotechniques 580–587 (1992)).

After injection an egg shell membrane patch (as described above) was placed over the top of the air cell. After the egg shell membrane dried OpSite tape (high MVP transparent dressing, #4008, Smith+Nephew, purchased from local pharmacy store) was used to bandage over the top of the egg shell membrane, and the eggs were returned to the Jamesway incubator to continue incubation. Embryos were transferred to a hatching basket on day 19 and hatched chicks were wing banded, dubbed and injected with SB-1/HVT Marek's disease vaccine (following the manufacturer's instructions).

Results

Flow cytometry (FC) analysis showed that about 35–45% of the blastodermal cells expressed the EMA-1 epitope after two weeks in culture. The size of EMA-1 positive cells ranged from 15–30 um.

Approximately 30% of the blastodermal cells remained EMA-1 positive after two months in culture. The cells were able to form embryonic stem cell-like colonies, yet exhibited EMA-1 epitope. These colonies were tightly compacted and uniform in morphology. These appear to be stable (under the culture conditions described below) primordial germ cells.

Without addition of the avian navel extract in the culture medium, the blastodermal cells replicated one time but could not survive longer than two weeks. With the turkey navel extract supplement in the medium the cells would replicate two to three times (depending on the line of egg source). Then the growth rate would slow down and the cells would attain dormancy for about four weeks. The dormancy period could be shortened to two weeks if turkey navel extract was added to the cultures on a daily basis.

After four weeks of dormancy the cells resumed replication, and they were subcultured. Collagenase solution was used to facilitate dissociation after revival from dormancy. Donor cells were used for cell injection/transplantation after two to six months in culture.

When extensively cultured BDC were transferred from a culture insert to a conventional tissue culture plate at low cell density ($10^3$ cells/cm$^2$) the BDC begin differentiating into fibroblast-like, melanocyte-like, neural cell-like, and muscle cell-like differentiated cells that could be morphologically identified (data not shown). This is indicative of pluripotency. Cell culture inserts under the culture medium conditions described herein allow BDC to absorb nutrients from above and below the porous membrane and this appears to prevent the spontaneous differentiation processes.

After BDC recovered from dormancy and resumed growth they were passaged three more times, incubated with DiI-C18 red dye, and injected into 18 hour embryos. In one experiment, six days after injection the embryonic tissues were removed and cryosectioned at 5 um thickness. Using fluorescent microscopy cells with red dye were detected in gonadal and other tissues. This indicated that cultured BDC were able to mature or differentiate into gonadal and various other embryonic tissues.

In another experiment, cultured BDC (two months or longer) were transfected with three plasmid/vectors (pGFP, pHCl or BFIV-class I) three times (once per 10 days) using a calcium phosphate precipitation method without drug selection. Three days after the last transfection the transfected BDC were removed from culture inserts and treated with collagenase solution to obtain a single cell suspension. The BDC suspension was resuspended in PBS containing 1% chicken serum and injected into 18 hour embryos in the germinal crescent area.

Hatchability following this injection procedure was 9.2% (donor cells were from Line 0 MHC=$B^{21}B^{21}$, recipient eggs were $15I_5 \times 7_1$ MHC=$B^2B^{15}$). Blood was obtained from the four week old progeny chickens and analyzed by flow cytometry. Donor chimeric B21B21 cells were detected in recipient B2B15 blood. In some chickens the percent of donor cells was as high as 25% to 33%.

Moreover, seven out of 49 putative chimera chickens had MHC antigen of the donor types of cells in the blood. The expression of class I antigen in transfected recipients was undetected in the peripheral blood of chickens. One of five transfected chickens expressed pHcl in the blood cells at about 4%. One of one transfected chickens expressed green fluorescent protein at 12%. Thus, foreign traits could be passed from the recombinant cell culture to living progeny poultry.

It will be appreciated that the present invention is believed to be suitable for use with all types of birds, but appears most commercially valuable for use with commercial poultry such as chickens, turkeys, pheasant, ducks, and geese.

The extract is preferably a water lysate fraction extract from embryonic avian (especially embryonic turkey) navel. However, similar extracts from other bird species should also work. The type of material in the extract that is likely to be responsible for conferring the properties specified herein is protein (e.g. likely growth factors such as cytokines).

The cell cultures are believed to contain primordial germ cells. However, they are best characterized by their expression of the EMA-1 antibody.

Even though the preferred embodiments have been described above, it will be appreciated by those skilled in the art that other modifications can be made within the scope of the invention. Thus, the claims should be looked to in order to judge the full scope of the invention.

Industrial Applicability

The invention provides avian primordial germ cell lines capable of long-term culture, as well as methods for maintaining and freezing these lines, materials useful in such methods, and birds created using these materials.

We claim:

1. A culture of undifferentiated avian blastoderm cells expressing the EMA-1 epitope and comprising isolate from avian navel, wherein the culture maintains its undifferentiated characteristic and expresses the EMA-1 epitope for more than two months.

2. The culture of claim 1, wherein the avian navel is embryonic avian navel.

3. The culture of claim 1, wherein the avian blastodermal cells are selected from the group consisting of turkey cells, duck cells, pheasant cells, geese cells, and chicken cells.

4. The culture of claim 2, wherein the culture maintains its undifferentiated characteristic and expresses the EMA-1 epitope for more than six months.

5. The culture of claim 2, wherein the avian navel is turkey navel and maintains its undifferentiated characteristic and expresses the EMA-1 epitope for more than two months.

6. A method of producing a sustained culture of undifferentiated blastodermal cells that expresses the EMA-1 epitope, comprising:

collecting avian cells from avian blastoderm prior to the formulation of a primitive streak;

and culturing the avian cells in the presence of isolate from avian navel.

7. The method of producing a sustained culture of claim 6, wherein the avian navel is embryonic avian navel.

8. The method of producing a sustained culture of claim 6, wherein the isolate is turkey navel extract.

9. A culture medium for culturing avian blastodermal cells which comprises an isolate from avian navel, inorganic salts, vitamins, amino acids, and water.

10. The culture medium of claim 9, wherein the avian navel is turkey navel.

11. A method of preserving an avian germ line genome, comprising freezing the culture of claim 1, wherein the avian germ line is preserved.

* * * * *